(12) United States Patent
Bartels et al.

(10) Patent No.: US 11,414,420 B2
(45) Date of Patent: Aug. 16, 2022

(54) PYRIMIDINE DERIVATIVES

(71) Applicant: Hoffmann-La Roche Inc., Little Falls, NJ (US)

(72) Inventors: Bjoern Bartels, Basel (CH); Xinlan Aloise Ford Cook, Oxford (GB); Hasane Ratni, Basel (CH); Michael Reutlinger, Basel (CH); Walter Vifian, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/767,084

(22) PCT Filed: Nov. 26, 2018

(86) PCT No.: PCT/EP2018/082504
§ 371 (c)(1),
(2) Date: May 26, 2020

(87) PCT Pub. No.: WO2019/101984
PCT Pub. Date: May 31, 2019

(65) Prior Publication Data
US 2020/0291032 A1    Sep. 17, 2020

(30) Foreign Application Priority Data

Nov. 27, 2017  (EP) ..................... 17203734

(51) Int. Cl.
| | |
|---|---|
| *A61K 31/517* | (2006.01) |
| *A61K 31/519* | (2006.01) |
| *C07D 239/70* | (2006.01) |
| *C07D 487/04* | (2006.01) |
| *C07D 403/12* | (2006.01) |

(52) U.S. Cl.
CPC ......... *C07D 487/04* (2013.01); *C07D 403/12* (2013.01)

(58) Field of Classification Search
CPC .. A61K 31/517; A61K 31/519; C07D 239/70; C07D 487/04
USPC .................... 514/258.1, 265.1; 544/253, 280
See application file for complete search history.

(56) References Cited

FOREIGN PATENT DOCUMENTS

| WO | 2011/014535 A1 | 2/2011 | |
|---|---|---|---|
| WO | 2015/153709 A1 | 10/2015 | |
| WO | WO-2019101984 A1 * | 5/2019 | ........... C07D 487/04 |

OTHER PUBLICATIONS

Jordan, V. C. Nature Reviews: Drug Discovery, 2, 2003, 205.*
Hackam, et al. JAMA, 296(14), 2006, 1731-1732.*
"International Preliminary Report on Patentability—PCT/EP2018/082504" (Report dated Jun. 2, 2020; Chapter I), :pp. 1-7 (dated Jun. 11, 2020).
"International Search Report—PCT/EP2018/082504" :pp. 1-11 (dated Jan 23, 2019).

* cited by examiner

*Primary Examiner* — Douglas M Willis
(74) *Attorney, Agent, or Firm* — Genentech, Inc.; Richard G. A. Bone

(57) ABSTRACT

The invention provides new pyrimidine compounds having the general formula (I), wherein $R^1$, $R^2$, $R^3$, n, and X are as described herein, compositions including the compounds, processes of manufacturing the compounds and methods of using the compounds.

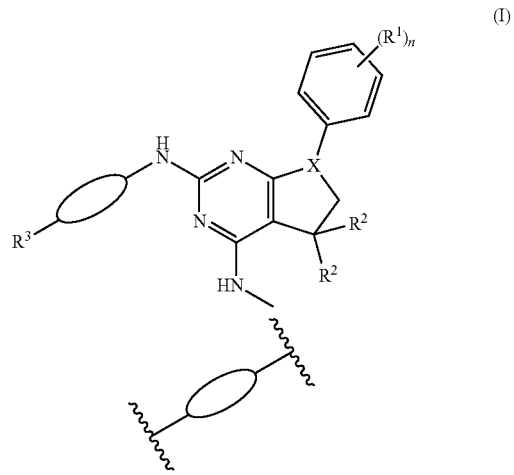

14 Claims, No Drawings

PYRIMIDINE DERIVATIVES

CROSS-REFERENCE TO RELATED APPLICATIONS

This application is a National Stage Entry of International Application No. PCT/EP2018/082504, filed Nov. 26, 2018, which claims benefit of priority to European Application No. 17203734.4 filed Nov. 27, 2017, each of which is incorporated herein by reference in its entirety.

FIELD OF THE INVENTION

The present invention relates to pyrimidine derivatives useful as γ-secretase modulators, their manufacture, pharmaceutical compositions comprising said compounds and their use as medicaments for the treatment of diseases associated with the deposition of β-amyloid in the brain, such as Alzheimer's disease, cerebral amyloid angiopathy, hereditary cerebral hemorrhage with amyloidosis-Dutch type (HCHWA-D), multi-infarct dementia, dementia pugilistica and Down syndrome.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain lengths, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, 525, pages 212-217). The presenilins are bearing the catalytic site and represent a group of atypical aspartyl protea-ses which cleave their substrates within the TM and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease. Therefore, it was believed that selective and potent inhibition of γ-secretase might be useful for the prevention and treatment of AD.

An alternative mode of treatment is the modulation of the γ-secretase activity which results in a selective reduction of the Aγ42 production. This will lead in an increase of shorter Aβ isoforms, such as Aβ38, Aβ37 or others, which have no or reduced capability for aggregation and plaque formation, and are not or less neurotoxic. Compounds which show this effect on modulating γ-secretase activity include certain non-steroidal anti-inflammatory drugs (NSAIDs) and related analogues (Weggen et al., Nature, 414 (2001) 212-16).

Numerous documents describe the current knowledge on γ-secretase modulation, for example the following publications:

Morihara et al, J. Neurochem., 83 (2002) 1009-12
Jantzen et al, J.Neuroscience, 22 (2002) 226-54
Takahashi et al, J. Biol. Chem., 278 (2003) 18644-70
Beher et al, J. Biol. Chem., 279 (2004) 43419-26
Lleo et al, Nature Med., 10 (2004) 1065-6
Kukar et al, Nature Med., 11 (2005) 545-50
Perretto et al, J. Med. Chem. 48 (2005) 5705-20
Clarke et al, J. Biol. Chem., 281 (2006) 31279-89
Stock et al, Bioorg. Med. Chem. Lett. 16 (2006) 2219-2223
Narlawar et al, J. Med. Chem. 49 (2006) 7588-91
Ebke et al, J. Biol. Chem., 286 (2011) 37181-86
Oehlich, Gijsen et al, J. Med. Chem., 54 (2011), 669-698
Li et al., Biochemistry, 52 (2013), 3197-3216
Hall et al, Progress in Med. Chem., 53 (2014) 101-145
Bursavich et al, J. Med. Chem., 59 (2016) 7389-7409

Therefore, modulating the γ-secretase activity is a promising therapeutic strategy for the treatment or prevention of diseases associated with the deposition of β-amyloid in the brain, such as Alzheimer's disease, cerebral amyloid angiopathy, hereditary cerebral hemorrhage with amyloidosis-Dutch type (HCHWA-D), multi-infarct dementia, dementia pugilistica and Down syndrome.

There is a need for new compounds, formulations, treatments and therapies to treat diseases and disorders associated with the deposition of β-amyloid in the brain. It is, therefore, an object of this invention to provide compounds useful for the treatment or prevention of such diseases and disorders with improved therapeutic properties.

SUMMARY OF THE INVENTION

In one aspect, the present invention relates to a compound of formula (I),

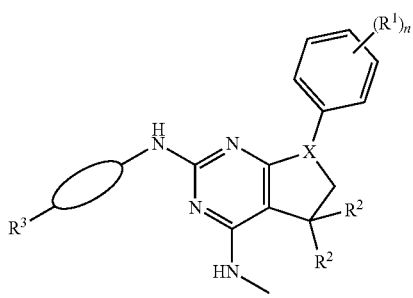

wherein each $R^1$ is independently selected from hydrogen and halogen;

n is 1, 2 or 3;

$R^2$ is hydrogen or methyl;

$R^3$ is a five membered heteroaryl group, selected from

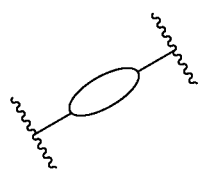

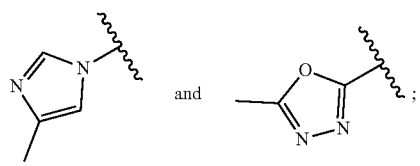

is a disubstituted bicyclo[1,1,1]pentane or disubstituted bicyclo[2,2,2]octane selected from

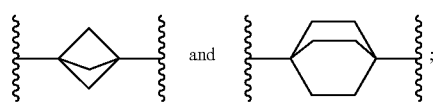 [SMILES: *C12CC(*)(C1)C2 ; *C12CCC(*)(CC1)CC2]

X is nitrogen or carbon;

or to a pharmaceutically acceptable salt thereof.

In a further aspect, a process for the preparation of a compound of formula (I) as described herein, comprising reacting a compound of formula 2

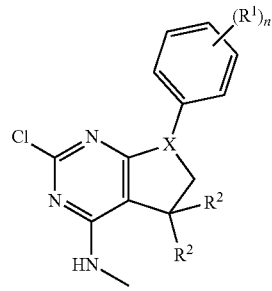

with a compound of formula 3

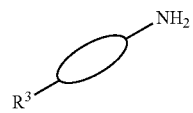

wherein $R^1$, $R^2$, $R^3$, n,

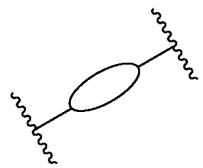

and X are as defined herein, to form said compound of formula (I), and if desired, converting the compound obtained into a pharmaceutically acceptable salt thereof.

In a further aspect, the present invention provides a compound of formula (I) as described herein, whenever prepared by a process as described above.

In a further aspect, the present invention provides a medicament containing one or more compounds of formula (I) as described herein and a pharmaceutically acceptable excipient.

In a further aspect, the present invention provides the use of a compound of formula (I) as described herein for the manufacture of a medicament for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In a further aspect, the present invention provides a compound of formula (I) as described herein for use as a therapeutically active substance.

In a further aspect, the present invention provides the use of a compound of formula (I) as described herein for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In a further aspect, the present invention provides a compound of formula (I) as described herein for use in the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In a further aspect, the present invention provides a method for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome, which method comprises administering an effective amount of a compound of formula (I) as defined herein.

DETAILED DESCRIPTION OF THE INVENTION

The following definitions of the general terms used in the present description apply irrespectively of whether the terms in question appear alone or in combination with other groups. The term "halogen" denotes chlorine, iodine, fluorine and bromine.

The term "pharmaceutically acceptable salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Compounds of the Invention

In a first aspect, the present invention provides a compound of formula (I)

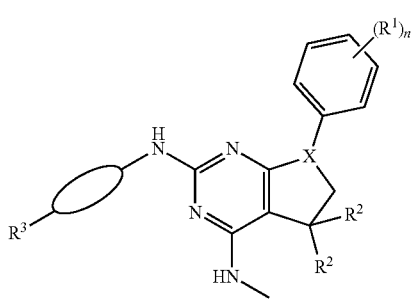

(I)

wherein
each $R^1$ is independently selected from hydrogen and halogen;
n is 1, 2 or 3;
$R^2$ is hydrogen or methyl;
$R^3$ is a five membered heteroaryl group, selected from

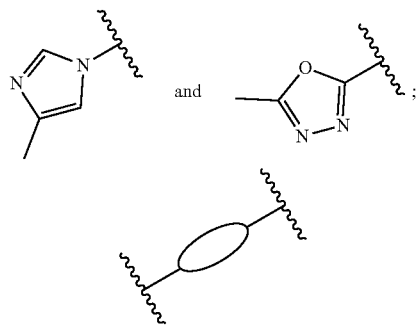

is a disubstituted bicyclo[1,1,1]pentane or disubstituted bicyclo[2,2,2]octane selected from

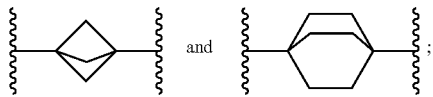 [SMILES: *C12CC(*)(C1)C2 ; *C12CCC(*)(CC1)CC2]

X is nitrogen or carbon;
or to a pharmaceutically acceptable salt thereof.

In one embodiment, there is provided a compound of formula (I) as described herein, wherein the compound of formula (I) is a compound of formula (I-a):

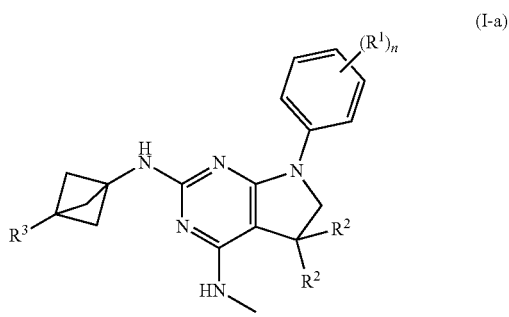

(I-a)

wherein
each $R^1$ is independently selected from hydrogen and halogen;
n is 1, 2 or 3;
$R^2$ is hydrogen or methyl;
$R^3$ is a five membered heteroaryl group, selected from

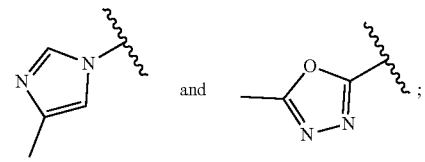

or a pharmaceutically acceptable salt thereof.

In one embodiment, there is provided a compound of formula (I-a) as described herein, selected from 7-(4-fluorophenyl)-N4,5,5-trimethyl-N2-[3-(5-methyl-1,3,4-oxadiazol-2-yl)-1-bicyclo[1.1.1]pentanyl1]-6H-pyrrolo[2,3-d]pyrimidine-2,4-diamine; 7-(4-fluorophenyl)-N4,5,5-trimethyl-N2-[3-(4-methylimidazol-1-yl)-1-bicyclo[1.1.1]pentanyl]-6H-pyrrolo[2,3-d]pyrimidine-2,4-diamine; 7-(4-fluorophenyl)-N4-methyl-N2-[3-(4-methylimidazol-1-yl)-1-bicyclo[1.1.1]pentanyl]-5,6-dihydropyrrolo[2,3-d]pyrimidine-2,4-diamine; 7-(3,5-difluorophenyl)-N4-methyl-N2-[3-(4-methylimidazol-1-yl)-1-bicyclo[1.1.1]pentanyl]-5,6-dihydropyrrolo[2,3-d]pyrimidine-2,4-diamine; 7-(2,4-difluorophenyl)-N4-methyl-N2-[3-(4-methylimidazol-1-yl)-1-bicyclo[1.1.1]pentanyl]-5,6-dihydropyrrolo[2,3-d]pyrimidine-2,4-diamine; 7-(3-chloro-5-fluoro-phenyl)-N4-methyl-N2-[3-(4-methylimidazol-1-yl)-1-bicyclo[1.1.1]pentanyl]-5,6-dihydropyrrolo[2,3-d]pyrimidine-2,4-diamine; N4-methyl-N2-[3-(4-methylimidazol-1-yl)-1-bicyclo[1.1.1]pentanyl]-7-(2,3,4-trifluorophenyl)-5,6-dihydropyrrolo [2,3-d]pyrimidine-2,4-diamine; 7-(2-fluorophenyl)-N4-methyl-N2-[3-(4- methylimidazol-1-yl)-1-bicyclo[1.1.1]pentanyl]-5,6-dihydropyrrolo[2,3-d]pyrimidine-2,4-diamine; 7-(2,3-difluorophenyl)-N4-methyl-N2-[3(4-methylimidazol-1-yl)-1-bicyclo[1.1.1]pentanyl]-5,6-dihydropyrrolo[2,3-d]pyrimidine-2,4-diamine; or a pharmaceutically acceptable salt thereof.

In another embodiment, there is provided a compound of formula (I) as described herein, wherein the compound of formula (I) is a compound of formula (I-b):

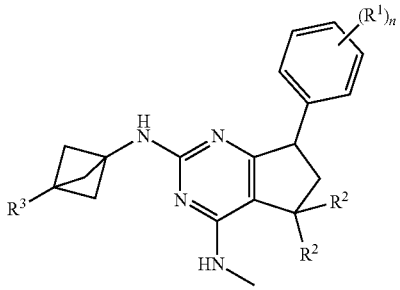

(I-b)

wherein each $R^1$ is independently selected from hydrogen and halogen;

n is 1, 2 or 3;

$R^2$ is hydrogen or methyl;

$R^3$ is a five membered heteroaryl group, selected from

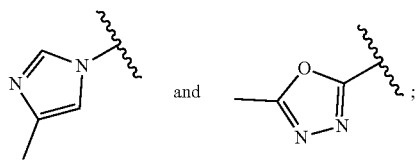

or a pharmaceutically acceptable salt thereof.

In a preferred embodiment, there is provided a compound of formula (I-b) as described herein, selected from (7R)-7-(4-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine; (7S)-7-(4-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine; (7R)-7-(3-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine; (7S)-7-(3-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine; or a pharmaceutically acceptable salt thereof.

In another embodiment, there is provided a compound of formula (I) as described herein, wherein the compound of formula (I) is a compound of formula (I-c):

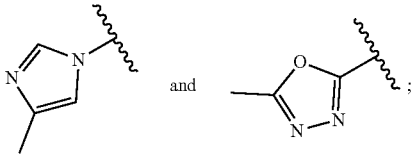

(I-c)

wherein each $R^1$ is independently selected from hydrogen and halogen;

n is 1, 2 or 3;

$R^2$ is hydrogen or methyl;

$R^3$ is a five membered heteroaryl group, selected from

or a pharmaceutically acceptable salt thereof.

In one embodiment, there is provided a compound of formula (I-c) as described herein, selected from 7-(4-fluorophenyl)-N4,5,5-trimethyl-N2-[4-(4-methylimidazol-1-yl)-1-bicyclo[2.2.2]octanyl]-6H-pyrrolo[2,3-d]pyrimidine-2,4-diamine; 7-(4-fluorophenyl)-N4-methyl-N2-[4-(4-methylimidazol-1-yl)-1-bicyclo[2.2.2]octanyl]-5,6-dihydropyrrolo[2,3-d]pyrimidine-2,4-diamine; or a pharmaceutically acceptable salt thereof.

In another embodiment, there is provided a compound of formula (I) as described herein, wherein the compound of formula (I) is a compound of formula (I-d):

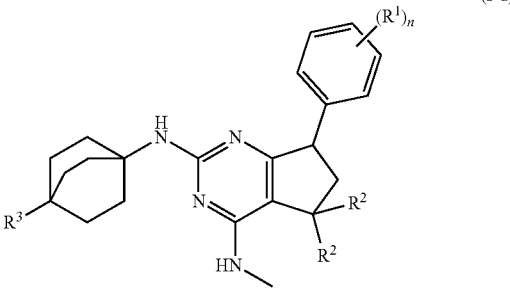

(I-d)

wherein
each $R^1$ is independently selected from hydrogen and halogen;
n is 1, 2 or 3;
$R^2$ is hydrogen or methyl;
$R^3$ is a five membered heteroaryl group, selected from

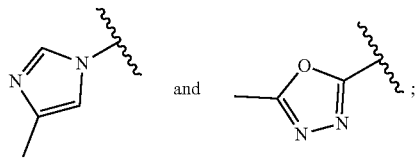

or a pharmaceutically acceptable salt thereof.

In one embodiment, there is provided a compound of formula (I-d) as described herein, selected from (7R)-7-(4-fluorophenyl)-N4-methyl-N2-[4-(4-methylimidazol-1-yl)-1-bicyclo[2.2.2]octanyl]-6,7-dihydro-5H-cyclopenta[d]pyrimidine-2,4-diamine; (7S)-7-(4-fluorophenyl)-N4-methyl-N2-[4-(4-methylimidazol-1-yl)-1-bicyclo[2.2.2]octanyl]-6,7-dihydro-5H-cyclopenta[d]pyrimidine-2,4-diamine; or a pharmaceutically acceptable salt thereof.

The compound of formula (I) may contain one or more asymmetric centers and can be present in the form of optically pure enantiomers, mixture of enantiomers such as, for example, racemates, mixtures of diastereoisomers, diastereoisomeric racemates or mixtures of diastereoisomeric racemates.

Processes of Manufacturing

Processes for the manufacture of compounds of formula (I) as described herein are also an object of the present invention.

The present compounds of formula (I) and their pharmaceutically acceptable salts can be prepared by methods known in the art.

In one embodiment, compounds of formula (I) as described herein may be prepared by a process comprising reacting a compound of formula 2

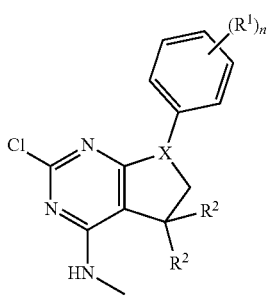

with a compound of formula 3

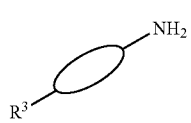

wherein $R^1$, $R^2$, $R^3$, n,

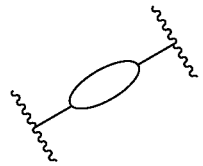

and X are as defined herein, to form said compound of formula (I), and if desired, converting the compound obtained into a pharmaceutically acceptable salt thereof.

In one embodiment, compounds of formula (I) and their intermediates may be prepared by schemes 1-4 and by the description of 17 specific examples.

General Synthesis of Compounds of Formula (I)

Scheme 1

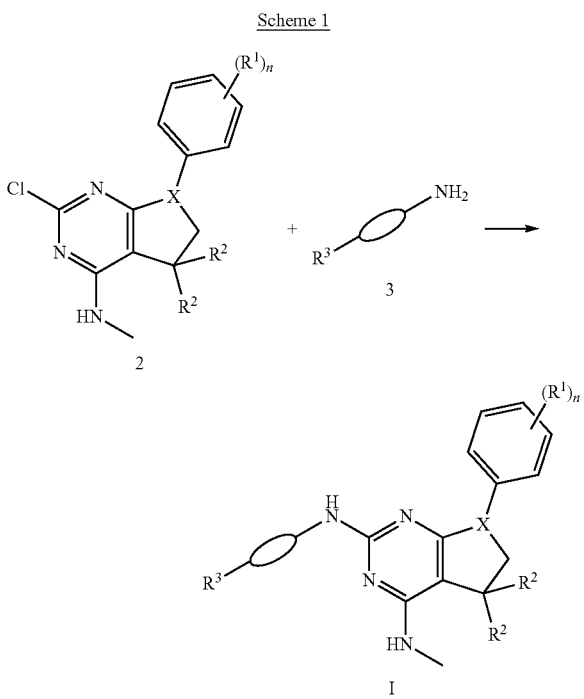

The preparation of compounds of formula (I) is made according to scheme 1. The synthesis of target compounds of formula (I) make use of a Buchwald type coupling between a chloropyrimidine derivative of formula 2 and an amino moiety of formula 3. This coupling is carried out in the presence of catalytic or stoichiometric amounts of a suitable transition metal complex, e.g. bis(dibenzylideneacetone)palladium(0), and, respectively, catalytic or stoichiometric amounts of a suitable phosphine ligand, e.g. 2-dicyclohexylphosphino-2'-(N,N-dimethylamino)biphenyl, and, furthermore, in the presence of a suitable base, e.g. alkali carbonate or alkaliphosphate, e.g. cesium carbonate. The reaction can be carried out in a polar, aprotic solvent, e.g. N-methylpyrrolidinone or dimethylformamide, at temperatures between 100° C. and 170° C., preferably between 140° C. and 160° C., optionally under microwave radiation in a closed vial.

General Synthesis of Intermediates of Type 2a (X is a N and R² is Methyl)

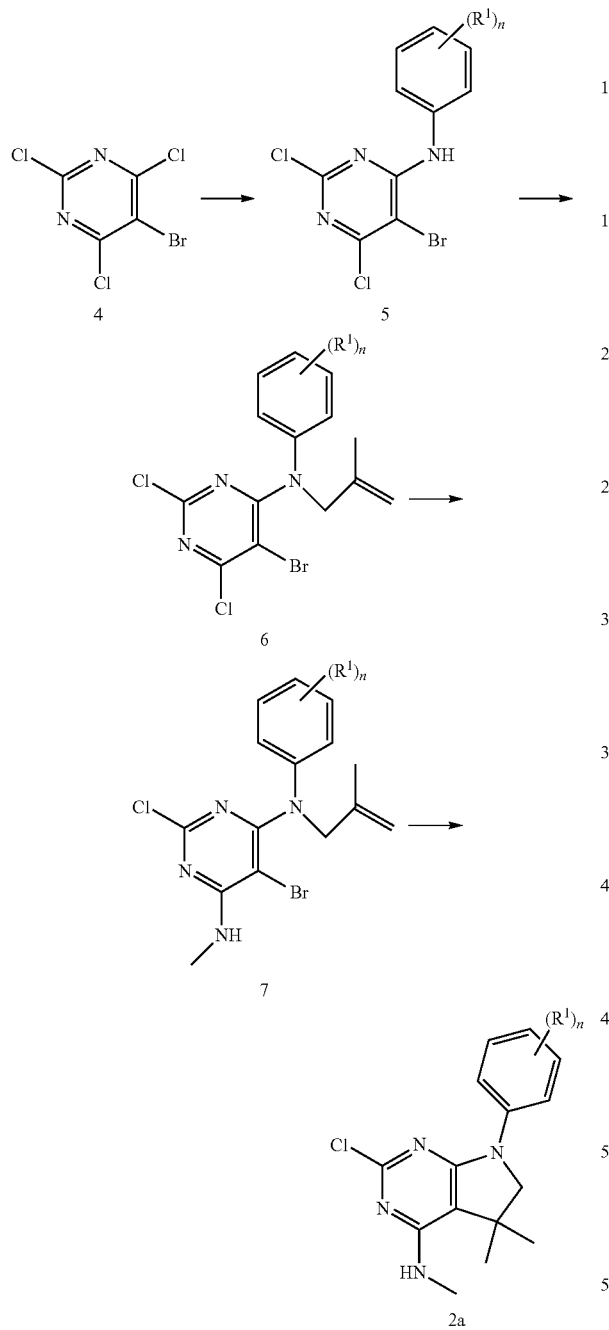

The intermediates of formula 2a, wherein R¹ and n are as defined above, can be prepared by methods known in the art. For example, intermediates of formula 2a, wherein R¹ and n are as defined above can be accessed using the synthetic sequence depicted in scheme 2. Pyrimidine 4, can be reacted with optionally substituted anilines in the presence of a non-nucleophilic base, such as sodium acetate or trialkylamine, e.g. triethyl amine or N,N-diisopropylethyl amine, or alkali hexamethyldisilazide, e.g. lithiumhexamethyldisilazide, in a suitable polar solvent, such as tetrahydrofuran, acetonitrile or dichloromethane. Thereafter, the intermediate of formula 5 can be reacted with an appropriate alkylating agent in the presence of a suitable non-nucleophilic base, e.g. sodium hydride, in a polar solvent, e.g. dimethylformamide or N-methylpyrrolidinone, at temperatures of 0° C. to 100° C., preferably between 30° C. and 60° C. Next, the intermediate of formula 6 can be converted into an intermediate of formula 7 by reaction with methylamine in an appropriate polar solvent, e.g. ethanol, tetrahydrofuran. The resulting mixture of regioisomers can be separated by chromatography or, alternatively, the mixture can be used in the next step and the resulting products separated at this stage. In the next step, the intermediate of formula 7 is cyclized to the intermediate of formula 2a by means of a Heck reaction. For example, the intermediate of formula 7 can be reacted with sub-stoichiometric or stoichiometric amounts of a suitable transition metal containing compound, e.g. palladium (II) acetate, optionally in the presence of a suitable phosphine ligand, for example triphenyl phosphine, furthermore in the presence of a suitable base, such as a trialkyl amine or an alkali carboxylate salt, e.g. triethyl amine or sodium formate. The reaction can take place in an appropriate polar solvent, e.g. dimethylformamide, N-methylpyrrolidinone, or methanol, optionally in the presence of a suitable tetraalkyl ammonium salt, e.g. tetrabutylammonium chloride, at elevated temperatures of 40° C. to 100° C., preferably 70° C. to 90° C.

General Synthesis of Intermediates of Type 2b (X is a C and R² is H)

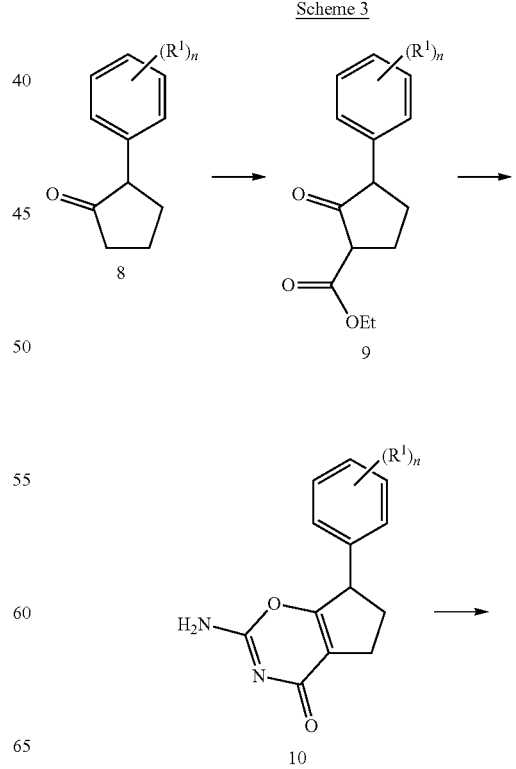

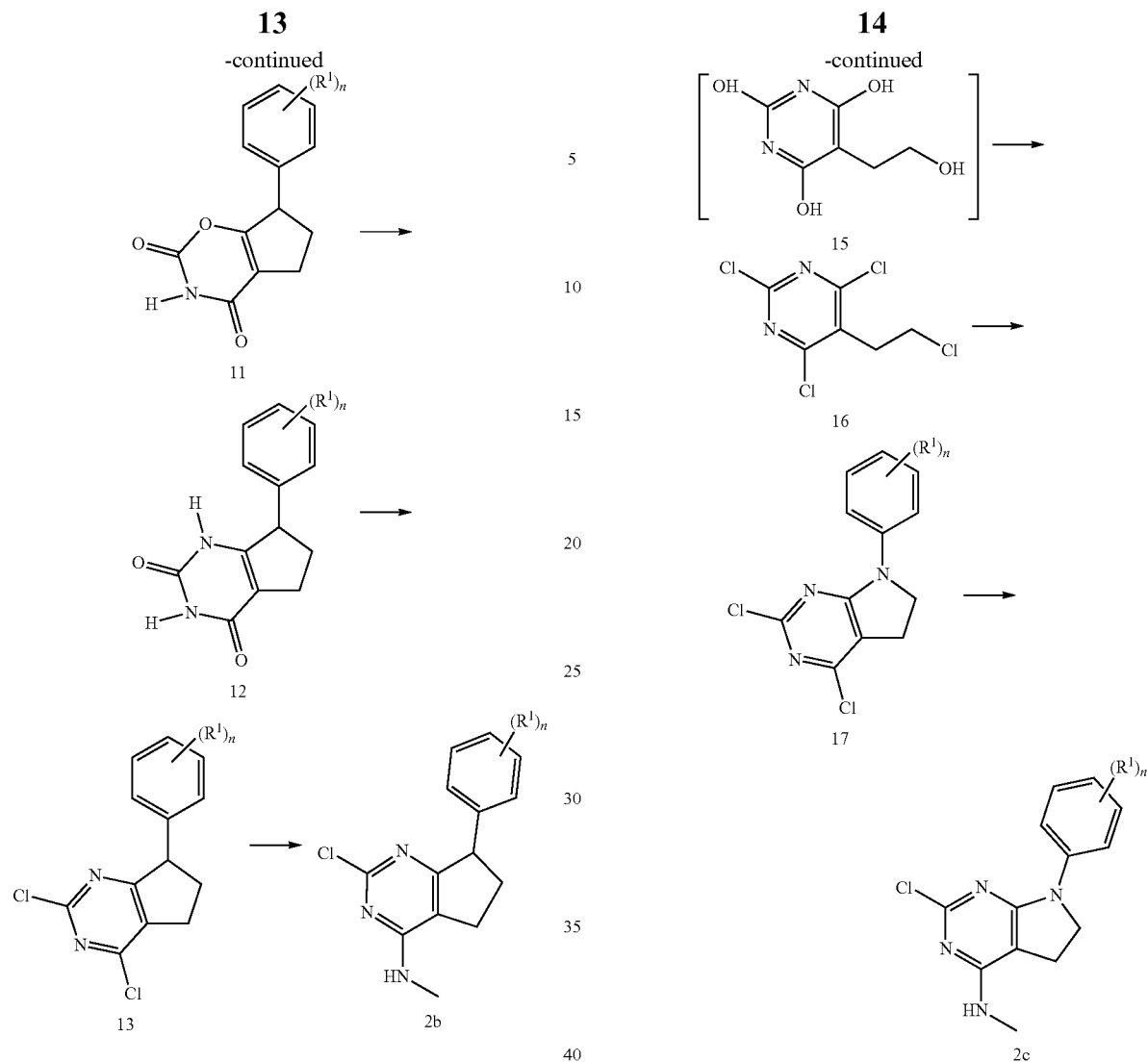

The preparation of intermediates of type 2b, wherein $R^1$ and n are as defined above, was carried out as shown in scheme 3 in a similar manner as described in WO2011/014535. The arylcyclopentanones 8 can be deprotonated with a strong base, such as LDA and treated with alkylcyanoformate to give the corresponding ketoesters 9, which upon reaction with 2-methyl-2-thiopseudourea provide 2-amino-7-aryl-6,7-dihydrocyclopenta[e][1,3]oxazin-4(5H)-ones 10. Acid-catalysed hydrolysis gave intermediates 11. Reaction with ammonia provides the pyrimidine diones 12 which are readily chlorinated to give intermediates 13. Finally, upon reacting with methyl amine, intermediates 2b are obtained.

General Synthesis of Intermediates of Type 2c (X is a N and $R^2$ is H)

Scheme 4

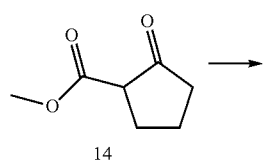

14

An intermediate of formula 2c, wherein $R^1$ and n are as defined above, can be synthesized according to the sequence depicted in scheme 4. A compound of formula 14, that is either commercially available or can be accessed as described, e.g., in EP2050749, can be reacted with urea in the presence of at least 1 equivalent, preferably, 2-3 equivalents of a suitable base, such as alkali aikoxide, e.g. sodium ethoxide, in an appropriate polar protic or aprotic solvent, e.g. ethanol, at elevated temperatures of 30° C. to 120° C., preferably 60° C. to 80° C. The crude product of formula 15, that can be isolated as sodium salt, can thereafter be reacted with a chlorinating agent, such as phosphorus oxychloride, phosphorus pentachloride, or thionyl chloride, optionally in the presence of stoichiometric amounts of N,N-dimethylaniline, at temperatures between 60° C. and 110° C., preferably between 90° C. and 100° C. The resulting intermediate of formula 16 can then be converted into the fused bicyclic intermediates of formula 17 by reaction with an optionally substituted aniline in the presence of a suitable base, such as trialkyl amine, e.g. diisopropylethyl amine or triethyl amine, in an appropriate polar, aprotic solvent, such as acetonitrile, at temperatures of 30° C. to 70° C., preferably 40° C. to 60° C. Finally, upon reacting with methyl amine, intermediates 2c are obtained.

In one aspect, the present invention provides a compound of formula (I) as described herein, when manufactured according to any one of the processes described herein.

Medicaments and Administration

Another object of the present invention is a medicament comprising one or more compounds of formula (I) as described herein and at least one pharmaceutically acceptable excipient.

The compounds of formula (I) and the pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions. The administration can also be effected topically, e.g. transdermal administration, or in form of eye drops or ear drops.

The compounds of formula (I) can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula (I) or a pharmaceutically acceptable salt thereof and a therapeutically inert carrier are also an object of the present invention, as is a process for their production, which comprises bringing one or more compounds of formula (I) and/or pharmaceutically acceptable salts and, if desired, one or more other therapeutically valuable substances into a galenical administration form together with one or more therapeutically inert carriers.

In accordance with the invention compounds of formula (I) as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration, the dosage for adults can vary from about 0.01 mg to about 1000 mg per day of a compound of formula (I) or of the corresponding amount of a pharmaceutically acceptable salt thereof. The daily dosage may be administered as single dose or in divided doses and, in addition, the upper limit can also be exceeded when this is found to be indicated.

The pharmaceutical compositions according to the invention may be prepared as follows.

Preparation of Pharmaceutical Compositions Comprising Compounds of the Invention Tablet Formulation (Wet Granulation)

|      |                        | mg/tablet |     |     |     |
| ---- | ---------------------- | --------- | --- | --- | --- |
| Item | Ingredients            | 5         | 25  | 100 | 500 |
| 1.   | Compound of formula (I)| 5         | 25  | 100 | 500 |
| 2.   | Lactose Anhydrous DTG  | 125       | 105 | 30  | 150 |
| 3.   | Sta-Rx 1500            | 6         | 6   | 6   | 30  |
| 4.   | Microcrystalline Cellulose | 30    | 30  | 30  | 150 |
| 5.   | Magnesium Stearate     | 1         | 1   | 1   | 1   |
|      | Total                  | 167       | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|      |                        | mg/capsule |     |     |     |
| ---- | ---------------------- | ---------- | --- | --- | --- |
| Item | Ingredients            | 5          | 25  | 100 | 500 |
| 1.   | Compound of formula (I)| 5          | 25  | 100 | 500 |
| 2.   | Hydrous Lactose        | 159        | 123 | 148 | —   |
| 3.   | Corn Starch            | 25         | 35  | 40  | 70  |
| 4.   | Talc                   | 10         | 15  | 10  | 25  |
| 5.   | Magnesium Stearate     | 1          | 2   | 2   | 5   |
|      | Total                  | 200        | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Indications

Also an object of the present invention is a compound of formula (I) as described herein for use as a therapeutically active substance.

As described above, compounds of formula (I) and their pharmaceutically acceptable salts are useful as γ-secretase modulators.

In one aspect, the present invention provides the use of a compound of formula (I) as described herein for the manufacture of a medicament for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In one embodiment, the present invention provides the use of a compound of formula (I) as described herein for the manufacture of a medicament for the treatment of Alzheimer's disease.

In a further aspect, the present invention provides a compound of formula (I) as described herein for use in the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In one embodiment, the present invention provides a compound of formula (I) as described herein for use in the treatment of Alzheimer's disease.

In a further aspect, the present invention provides the use of a compound of formula (I) as described herein for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome.

In one embodiment, the present invention provides the use of a compound of formula (I) as described herein for the treatment of Alzheimer's disease.

In a further aspect, the present invention provides a method for the treatment of Alzheimer's disease, cerebral amyloid angiopathy, hereditary cerebral hemorrhage with amyloidosis-Dutch type (HCHWA-D), multi-infarct dementia, dementia pugilistica or Down syndrome, which method comprises administering an effective amount of a compound of formula (I) as described herein.

In one embodiment, the present invention provides a method for the treatment of Alzheimer's disease, which method comprises administering an effective amount of a compound of formula (I) as described herein.

EXAMPLES

The following examples are provided for illustration of the invention. They should not be considered as limiting the scope of the invention, but merely as being representative thereof.

1) Preparative Examples 1.1) General
Analytical Methods:
a) HPLC (method LCMS_fastgradient)
Column: Agilent Zorbax Eclipse Plus C18, Rapid Resolution HT, 2.1×30 mm, 1.8 µm
Solvent A: Water 0.01% Formic Acid; Solvent B: acetonitrile (MeCN)
Gradients:

| Time [min] | Flow Rate [ml/min] | % A | % B |
|---|---|---|---|
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 | b) $^1$H NMR
$^1$H NMR data are given in the following format: chemical shift in ppm (multiplet, coupling constants if applicable, integral). Abbreviations for multiplets: s, singlet; d, dublet; t, triplet; q, quartet; hept, heptet; m, multiplet. The chemical shifts are referenced to the respective deuterated solvent, CDCl$_3$ (7.27 ppm) or d6-DMSO (2.50 ppm).

Abbreviations:
The following abbreviations were used in the experimental part:
DMF=dimethylformamide;
DMSO=dimethyl sulfoxide;
EtOAc=ethyl acetate;
Et$_3$N=triethylamine;
FCS=fetal calf serum;
HPLC=high-performance liquid chromatography;
IMDM=Iscove's modified Dulbecco's medium;
iPr$_2$NEt=N,N-diisopropylethylamine;
MS=mass spectrum;
MTBE=TBME=methyl-tert-butylether;
NMP=N-methyl-2-pyrrolidone;
TFA=trifluoroacetic acid;
THF=tetrahydrofuran;
TLC=thin layer chromatography;
RT=room temperature, 20-25° C.

1.2) Preparation of Intermediates
1.2.1) Intermediates of Type 2a (according to Scheme 2)

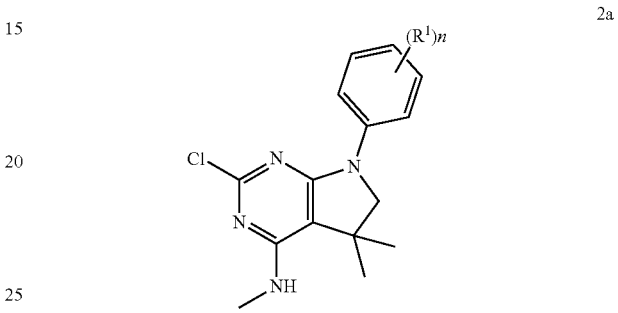

Intermediate 2a-1:

2-Chloro-7-(4-fluorophenyl)-N,5,5-trimethyl-6H-pyrrolo[2,3-d]pyrimidin-4-amine

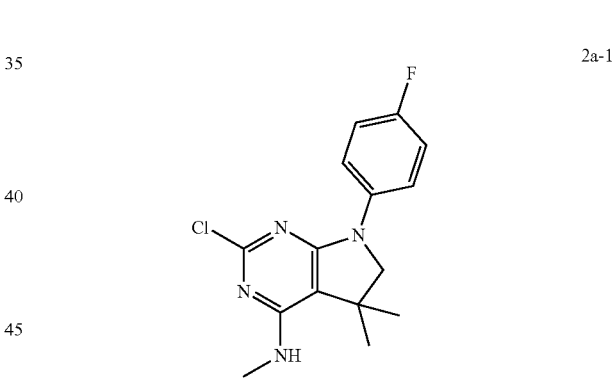

Step 1:

5-Bromo-2,6-dichloro-N-(4-fluorophenyl)pyrimidin-4-amine

5-Bromo-2,4,6-trichloropyrimidine (1.880 g, 6.81 mmol) was dissolved in THF (11 mL) and water (5 mL), and sodium acetate (1.68 g, 20.4 mmol), followed by 4-fluoroaniline (787 mg, 0.68 mL, 6.87 mmol) were added. The mixture was stirred at room temperature for 18 h. After that, a saturated aqueous solution of sodium hydrogenocarbonate (15 mL) was added and the resulting mixture was extracted with ethyl acetate (2×150 mL). The combined organic layers were dried (sodium sulfate) and concentrated in vacuo. The crude was purified by column chromatography (silica gel, 40 g, eluting with ethyl acetate/n-heptane, gradient 0:100 to 10:90) to afford, after drying in vacuo (40° C., 5 mbar), the title compound as a light brown solid (2.07 g, 90%). MS (ES+) m/z 335.9, 337.9, 339.9 [M+H, Br & 2 Cl isotopes].

Step 2:

5-Bromo-2,6-dichloro-N-(4-fluorophenyl)-N-(2-methylallyl)pyrimidin-4-amine

5-Bromo-2,6-dichloro-N-(4-fluorophenyl)pyrimidin-4-amine (1.45 g, 4.3 mmol) was dissolved in dimethylformamide (14 mL) and sodium hydride (60% dispersion in mineral oil, 239 mg, 5.98 mmol) was added carefully (gas evolution). The mixture was stirred at room temperature for 1 h. Then, 3-bromo-2-methylprop-1-ene (964 mg, 6.93 mmol) was added and the resulting mixture was stirred for 18 h at room temperature. After that, water (20 mL) was added, the mixture was extracted with methyltertbutyl ether (2×150 mL), the organic phases were washed with water (3×20 mL) and brine (20 mL), combined, dried (sodium sulfate), and concentrated in vacuo. The crude product was purified by column chromatography (silica gel, 120 g, eluting with ethyl acetate/n-heptane, gradient 0:100 to 5:95) to give the title compound as yellow oil (1.294 g, 69%). MS (ES+) m/z 390.0, 392.0, 394.0 [M+H, Br & 2 Cl isotopes].

Step 3:

5-Bromo-2-chloro-N4-(4-fluorophenyl)-N6-methyl-N4-(2-methylallyl)pyrimidine-4,6-diamine 5-Bromo-2,6-dichloro-N-(4-fluorophenyl)-N-(2-methylallyl)pyrimidin-4-amine (0.830 g, 1.91 mmol) was dissolved in tetrahydrofuran (1.9 mL) and a solution of methylamine in tetrahydrofuran (2.0 M, 3.8 mL, 7.6 mmol) was added dropwise. The mixture was stirred at room temperature for 18 h. After that, water (10 mL) was added, the mixture was extracted with ethyl acetate (2×90 mL), the organic layers were washed with brine (50 mL), combined, dried (sodium sulfate) and concentrated in vacuo. The crude product was purified by column chromatography (silica gel, 40 g, eluting with ethyl acetate/n-heptane, gradient 0:100 to 5:95) to afford the title compound as an off-white solid (396 mg, 51%). MS (ES+) m/z 385.0, 387.0, 389.0 [M+H, Br & Cl isotopes].

Step 4:

2-Chloro-7-(4-fluorophenyl)-N,5,5-trimethyl-6,7-dihydro-5H-pyrrolo[2,3-d] pyrimidin-4-amine 5-Bromo-2-chloro-N4-(4-fluorophenyl)-N6-methyl-N4-(2-methylallyl)pyrimidine-4,6-diamine (390 mg, 1.01 mmol), sodium formate (73 mg, 1.07 mmol), tetrabutylammonium chloride (287 mg, 1.03 mmol) and palladium (II) acetate (52 mg, 0.232 mmol) were charged under argon in a 25 mL round bottomed flask. Dimethylformamide (3.2 mL), followed by triethylamine (261 mg, 2.58 mmol) were added and the flask was evacuated carefully and backfilled with argon. The resulting mixture was stirred at 80° C. for 18 h. After cooling, water (5 mL) was added, the mixture was extracted with methyltertbutyl ether (2×60 mL), the organic layers were washed with water (3×10 mL) and brine (1×10 mL), combined, dried (sodium sulfate) and concentrated in vacuo. The crude product was purified by column chromatography (silica gel, 25 g, eluting with ethyl acetate/n-heptane, gradient 0:100 to 20:80) to afford the title compound as a yellow solid (259 mg, 83%). MS (ES+) m/z 307.1, 309.1 [M+H, Cl isotopes].

1.2.2) Intermediates of type 2b (according to scheme 3)

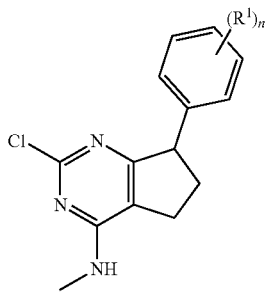

Intermediate 2b-1:

2-chloro-7-(4-fluorophenyl)-N-methyl-6,7-dihydro-5H-cyclopenta[d]pyrimidin-4-amine

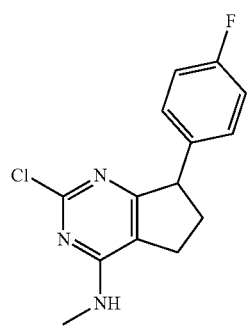

This intermediate was prepared as described in WO2011/014535.

Intermediate 2b-2:

2-chloro-7-(3-fluorophenyl)-N-methyl-6,7-dihydro-5H-cyclopenta[d]pyrimidin-4-amine

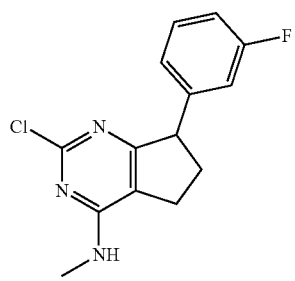

In analogy to the preparation of the intermediate 2b-1, from 2-(3-fluorophenyl) cyclopentanone was prepared the title compound 2b-2 as a white solid MS (ES+) m/z 278.09 [M+H].

1.2.3) Intermediates of Type 2c (according to scheme 4)

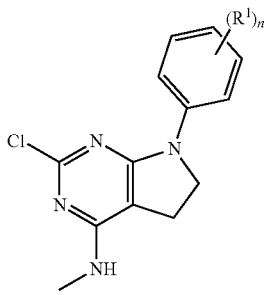

Intermediate 2c-1:

2-chloro-7-(4-fluorophenyl)-N-methyl-5,6-dihydro-pyrrolo[2,3-d]pyrimidin-4-amine

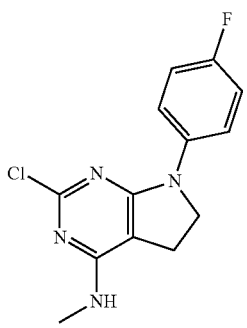

Step 1:

2,4,6-Trichloro-5-(2-chloroethyl)pyrimidine

Methyl 2-oxotetrahydrofuran-3-carboxylate (5.20 g, 36.1 mmol) was dissolved in ethanol (40 mL) and urea (2.17 g, 36.1 mmol) was added, followed by a solution of sodium ethoxide in ethanol (21% m/m, 24.3 g, 28 mL, 75 mmol). The resulting suspension was stirred at 75° C. for 18 h. After that, it was cooled to room temperature and concentrated in vacuo. The residue, a light brown solid (8.87 g), was added carefully in small portions to precooled (0-5° C., ice bath) phosphorus oxychloride (57.6 g, 35 mL). Strong fuming was observed. After that, N,N-dimethylaniline (5.74 g, 47.3 mmol) was added and the reaction mixture was stirred at 100° C. for 18 h. Then, it was cooled to room temperature, poured into ice water (480 g) and stirred for 1 h, until the ice was melted. The formed precipitate was filtered off, washed with water and dried in vacuo to afford the title compound as a dark brown solid (3.8 g, 43%), that was used without further purification in the next step.

$^1$H NMR (DMSO-d6, 300 MHz): δ 3.31 (t, J=7.2 Hz, 2 H), 3.86 (t, J=7.2 Hz, 2 H).

Step 2:

2,4-Dichloro-7-(4-fluorophenyl)-6,7-dihydro-5H-pyrrolo[2,3-d]pyrimidine 2,4,6-Trichloro-5-(2-chloroethyl)pyrimidine (1.84 g, 7.48 mmol) was dissolved in acetonitrile (40 mL), and 4-fluoroaniline (833 mg, 7.5 mmol), followed by N,N-diisopropylethylamine (2.0 g, 2.7 mL, 15.5 mmol) were added dropwise. The mixture was stirred at room temperature for 7 h and at 50° C. for 18 h. Then, it was concentrated in vacuo and the resulting crude product was purified directly by column chromatography (silica gel, 80 g, eluting with dichloromethane/n-heptane, gradient 0:100 to 80:20) to give a yellow solid, which was further triturated with a mixture of ethyl acetate/n-heptane (1:4, v/v) to afford, after filtration and drying in vacuo, the title compound as an off-white solid (893 mg, 42%).

$^1$H NMR (CDCl$_3$, 300 MHz): δ 3.19 (dd, J=8.3, 9.1 Hz, 2 H), 4.20 (dd, J=8.3, 9.1 Hz, 2 H), 7.12 (dd, J=8.1, 9.3 Hz, 2 H), 7.67 (dd, J=4.6, 9.3 Hz, 2 H). MS (ES+) m/z 284.1, 286.0 [M+H, 2 Cl isotopes].

Step 3:

2-chloro-7-(4-fluorophenyl)-N-methyl-5,6-dihydro-pyrrolo[2,3-d]pyrimidin-4-amine A solution of 2,4-dichloro-7-(2,3,4-trifluorophenyl)-6,7-dihydro-5H-pyrrolo[2,3-d]pyrimidine (1.90 g, 5.94 mmol, Eq: 1) and methyl amine ~8 M in ethanol (11.1 mL, 89 mmol, Eq: 15) in a sealed vial was heated in a microwave at 100° C. for 20 minutes. After cooling down to RT, the resulting precipitate was collected by filtration and washed with cold ethanol, then Et$_2$O and dried under vacuo. The two regioisomeres were separated by column chromatography (silica gel, eluting with ethyl acetate/n-heptane, gradient 30:70 to 100) to afford the title compound as an off-white solid (162 mg, 8%). MS (ES+) m/z 279.08 [M+H].

Intermediate 2c-2:

2-chloro-7-(3,5-difluorophenyl)-N-methyl-5,6-dihydropyrrolo[2,3-d]pyrimidin-4-amine

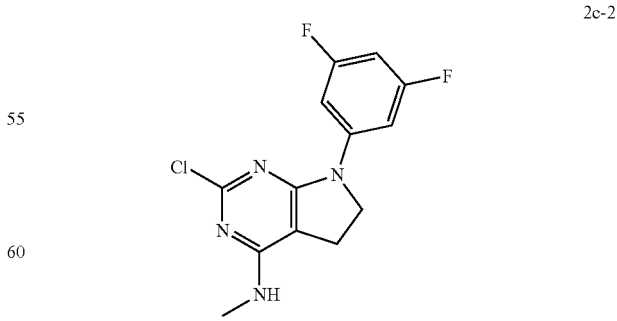

In analogy to the preparation of the intermediate 2c-1, using 3,5-difluoroaniline, the title compound was prepared as a white solid. MS (ES+) m/z 297.07 [M+H].

Intermediate 2c-3:

2-chloro-7-(2,4-difluorophenyl)-N-methyl-5,6-dihydropyrrolo[2,3-d]pyrimidin-4-amine

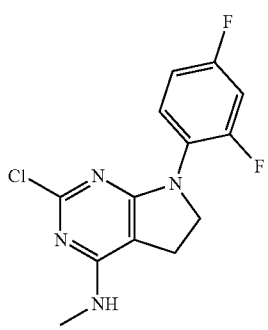

In analogy to the preparation of the intermediate 2c-1, using 2,4-difluoroaniline, the title compound was prepared as a white solid. MS (ES+) m/z 297.2 [M+H].

Intermediate 2c-4:

2-chloro-7-(3-chloro-5-fluoro-phenyl)-N-methyl-5,6-dihydropyrrolo[2,3-d]pyrimidin-4-amine

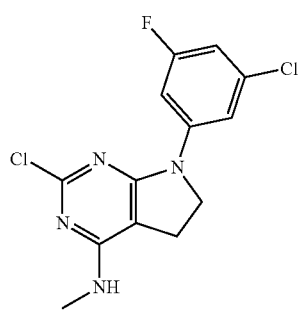

In analogy to the preparation of the intermediate 2c-1, using 3-chloro-5-fluoro-aniline, the title compound was prepared as a white solid. MS (ES+) m/z 313.2, 315.2 [M+H, Cl isotopes].

Intermediate 2c-5:

2-chloro-N-methyl-7-(2,3,4-trifluorophenyl)-5,6-dihydropyrrol[2,3-]pyrimidin-4-amine

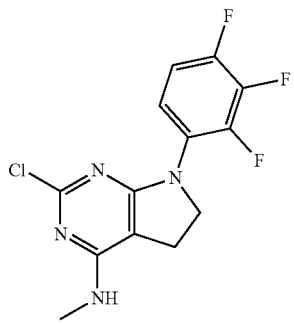

In analogy to the preparation of the intermediate 2c-1, using 2,3,4-trifluoroaniline, the title compound was prepared as a white solid. MS (ES+) m/z 315.19 [M+H].

Intermediate 2c-6:

2-chloro-7-(2-fluorophenyl)-N-methyl-5,6-dihydropyrrolo[2,3-d]pyrimidin-4-amine

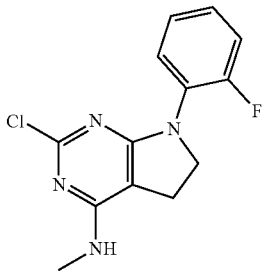

In analogy to the preparation of the intermediate 2c-1, using 2-fluoroaniline, the title compound was prepared as a white solid. MS (ES+) m/z 279.2 [M+H].

Intermediate 2c-7:

2-chloro-7-(2,3-difluorophenyl)-N-methyl-5,6-dihydropyrrolo[2,3-d]pyrimidin-4-amine

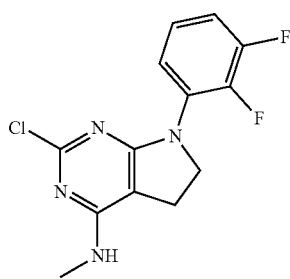

In analogy to the preparation of the intermediate 2c-1, using 2,3-difluoroaniline, the title compound was prepared as a white solid. MS (ES+) m/z 297.2 [M+H].

1.2.4) Intermediates of Ttype 3

Intermediate 3-1:

3-(5-methyl-1,3,4-oxadiazol-2-yl)bicyclo[1.1.1]pentan-1-amine

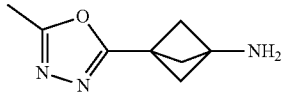

3-1

Step 1:

methyl 3-(tert-butoxycarbonylamino)bicyclo[1.1.1]pentane-1-carboxylate

Methyl 3-aminobicyclo[1.1.1]pentane-1-carboxylate hydrochloride (1.05 g, 5.91 mmol), Boc-anhydride (1.42 g, 1.51 mL, 6.5 mmol) and iPr$_2$NEt (3.82 g, 5.16 mL, 29.6 mmol) were combined in THF (30 mL) to yield a pale orange suspension. The reaction was stirred at RT for 4 hours, concentrated under vacuo, redissolved in EtOAc (50 mL) and washed with an aqueous solution of saturated NaHCO$_3$ (25 mL), then with a 3% citric acid solution (25 mL) and then brine (25 mL). The organic phase was dried over Na$_2$SO$_4$, and concentrated. The residue was purified by column chromatography (Heptane/EtOAc) to afford the title product (1.20 g, 84%) as a white solid. MS (ES+) m/z 186.1 [M-tBu)].

Step 2:

tert-Butyl N-[3-(hydrazinecarbonyl)-1-bicyclo[1.1.1]pentanyl]carbamate

Hydrazine hydrate (80% in H$_2$O, 2.6 g, 2.53 mL, 41.5 mmol) was added to methyl 3-(tert-butoxycarbonylamino)bicyclo[1.1.1]pentane-1-carboxylate (0.77 g, 3.19 mmol) in MeOH (5 mL) to give a white suspension, which became a pale yellow solution upon heating at 80° C. After 15 minutes, the reacton mixture was cooled down to RT, concentrated under vacuo and dired under high vacuum overnight to give the title product (0.77 g) which was used in the next step without further purification. MS (ES+) m/z 242.2 [M+H].

Step 3:

tert-Butyl N-[3-(5-methyl-1,3,4-oxadiazol-2-yl)-1-bicyclo[1.1.1]pentanyl]carbamate tert-Butyl N-[3-(hydrazinecarbonyl)-1-bicyclo[1.1.1]pentanyl]carbamate (0.77 g, 3.19 mmol) was suspended in EtOAc (14 mL). Acetic acid (230 mg, 0.219 mL, 3.83 mmol), Et$_3$N (1.29 g, 1.78 mL, 12.8 mmol) and propylphosphonic anhydride solution (50 wt. % in EtOAc, 5.08 g, 4.75 mL, 7.98 mmol) were added to the solution with stirring, forming a pale yellow solution (exothermic reaction). The reaction was heated in a microwave at 100° C. for 15 minutes, and then at 140° C. for 30 minutes. After cooling down to RT, the mixture was concentrated under vacuo, redissolved in EtOAc (40 mL) and washed with water (10 mL). The organic phase was dried over Na$_2$SO$_4$, filtered and concentrated. Column chromatography (Heptane/EtOAc) afforded the title compound (0.73 g, 87%) as an off-white solid. MS (ES+) m/z 266.2 [M+H].

Step 4:

3-(5-methyl-1,3,4-oxadiazol-2-yl)bicyclo[1.1.1]pentan-1-amine

Trifluoroacetic acid (6.34 g, 4.29 mL, 55.6 mL) was added to tert-Butyl N-[3-(5-methyl-1,3,4-oxadiazol-2-yl)-1-bicyclo[1.1.1]pentanyl]carbamate (0.73 g, 2.78 mmol) in CH$_2$Cl$_2$ (20 mL) at RT. After one hour, volatiles were removed under vacuo and the residue redissolved in CH$_2$Cl$_2$. The organic phase was washed with a saturated solution of NaHCO$_3$, dried over Na$_2$SO$_4$, concentrated and dried under high vacuum to give the title compound (0.36 g, 79%) as a white solid. MS (ES+) m/z 166.1 [M+H].

Intermediate 3-2:

3-(4-methylimidazol-1-yl)bicyclo[1.1.1]pentan-1-amine

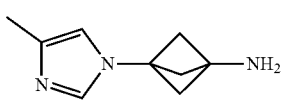

3-2

Step 1:

tert-butyl N-[3-(acetonylamino)-1-bicyclo[1.1.1]pentanyl]carbamate

Potassium iodide (0.15 g, 0.92 mmol) and cesium carbonate (1.50 g, 4.61 mmol) were added to tert-butyl N-(3-amino1-bicyclo[1.1.1]pentanyl)carbamate (0.96 g, 4.61 mmol) in solution in DMF (20 mL). The mixture was cooled to 0° C. and 1-chloropropan-2-one (0.49 g, 5.07 mmol) in solution in DMF (5 mL) was added. Stirring was continued overnight while the temperature was raising to RT. The mixture was filtered, and concentrated under vacuo. Column chromatography (1% to 10% MeOH in TBME) gave the title compound (0.68 g, 58%) as a light brown foam. MS (ES+) m/z 255.2 [M+H].

Step 2:

tert-butyl N-[3-[acetonyl(formyl)amino]-1-bicyclo[1.1.1]pentanyl]carbamate

Acetic anhydride (1.01 g, 0.93 mL, 9.88 mmol) was added to formic acid (1.79 g, 1.50 mL, 39 mmol) and stirred for 1 hour. A solution of tert-butyl N-[3-(acetonylamino)-1-bicyclo[1.1.1]pentanyl]carbamate (0.66 g, 2.60 mmol) in THF (12 mL) was added. The resulting dark solution was stirred for 30 minutes and then poured into H$_2$O (30 mL). EtOAc (50 mL) was added and the biphase mixture was stirred and the pH adjusted to 8-9 by addition of NaHCO$_3$ in small portions. The organic phase was then separated, dried over Na$_2$SO$_4$ and concentrated under vacuo. A column chromatography (30% to 100% EtOAc in Heptane) gave the title compound (0.33 g, 45%) as a brown foam. MS (ES+) m/z 283.1 [M+H].

Step 3:

tert-butyl N-[3-(4-methylimidazol-1-yl)-1-bicyclo[1.1.1]pentanyl]carbamate

To a solution of tert-butyl N[3-[acetonyl(formyl)amino]-1-bicyclo[1.1.1]pentanyl] carbamate (0.33 g, 1.17 mmol) in acetic acid (4 mL) was added ammonium acetate (0.45 g, 5.84 mmol). The reaction mixture was heated at 100° C. for 10 hours before a second portion of ammonium acetate (0.45 g, 5.84 mmol) was added and stiffing continued for another 4 hours. The volatiles were removed under vacuo, and a column chromatography (3% to 50% 2N NH$_3$/MeOH in TBME) gave the title product (0.096 g, 31%) as an off-white solid which was used directly in the next step.

Step 4:

3-(4-methylimidazol-1-yl)bicyclo[1.1.1]pentan-1-amine

To a solution of tert-butyl N-[3-(4-methylimidazol-1-yl)-1-bicyclo[1.1.1]pentanyl] carbamate (0.096 g, 0.365 mmol) in CH$_2$Cl$_2$ (2 mL) was added TFA (0.88 g, 0.60 mL, 7.78 mmol) and the mixture stirred overnight at RT. The volatiles were removed under vacuo, the residue redissolved in MeOH (2 mL) and an aqueous solution of NH$_4$OH (25%, 0.5 mL) followed by diatomaceous earth material isolute HM-N (3 g) were added. The mixture was concentrated and a column chromatography (2% to 15% of 2N NH3/MeOH in CH$_2$Cl$_2$) gave the title product (0.032 g, 16%) as a viscous colorless oil. MS (ES+) m/z 164.1 [M+H].

Intermediate 3-3:

4-(4-methylimidazol-1-yl)bicyclo[2.2.2]octan-1-amine hydrochloride

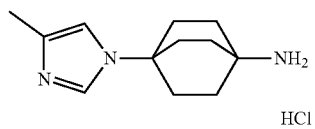

3-3

Step 1:

tert-butyl N-[4-(acetonylamino)-1-bicyclo[2.2.2]octanyl]carbamate

Potassium iodide (0.13 g, 0.78 mmol) and cesium carbonate (3.82 g, 11.7 mmol) were added to tert-butyl N-(4-amino-1-bicyclo[2.2.2]octanyl)carbamate (0.94 g, 3.91 mmol) in solution in DMF (6 mL). The mixture was cooled to 0° C. and 1-chloropropan-2-one (0.90 g, 9.78 mmol) in solution in DMF (5 mL) was added. Stirring was continued for 2 hours at 40° C. The mixture was filtered, and concentrated under vacuo. Column chromatography (0% to 7% 2N NH$_3$/MeOH in CH$_2$C$_{12}$) gave the title compound (0.32 g, 27%) as a light orange solid. MS (ES+) m/z 297.2 [M+H].

Step 2:

tert-butyl N-[4-[acetonyl(formyl)amino]-1-bicyclo[2.2.2]octanyl]carbamate

Acetic anhydride (0.42 g, 0.39 mL, 4.1 mmol) was added to formic acid (0.74 g, 0.63 mL, 16.2 mmol) and stirred for 1 hour. A solution of tert-butyl N-[4-(acetonylamino)-1-bicyclo[2.2.2]octanyl]carbamate (0.32 g, 1.08 mmol) in THF (8 mL) was added. The resulting dark solution was stirred for 30 minutes and then poured into H$_2$O (30 mL). EtOAc (50 mL) was added and the biphase mixture was stirred and the pH adjusted to 8-9 by addition of NaHCO$_3$ in small portions. The organic phase was then separated, dried over Na$_2$SO$_4$ and concentrated under vacuo. A column chromatography (30% to 100% EtOAc in Heptane) gave the title compound (0.29 g, 82%) as a brown foam. MS (ES+) m/z 325.2 [M+H].

Step 3:

tert-butyl N-[4-(4-methylimidazol-1-yl)-1-bicyclo[2.2.2]octanyl]carbamate

To a solution of tert-butyl N[4-[acetonyl(formyl)amino]-1-bicyclo[2.2.2]octanyl] carbamate (0.29 g, 0.89 mmol) in acetic acid (4 mL) was added ammonium acetate (0.34 g, 4.47 mmol). The reaction mixture was heated at 100° C. overnight and a second portion of ammonium acetate (0.14 g, 1.82 mmol) was added and stiffing continued for another 14 hours. The volatiles were removed under vacuo, and a column chromatography (0% to 10% 2N NH$_3$/MeOH in TBME) gave the title product (0.072 g, 26%) as an off-white solid. MS (ES+) m/z 306.2 [M+H].

Step 4:

4-(4-methylimidazol-1-yl)bicyclo[2.2.2]octan-1-amine, hydrochloride

To a suspension of tert-butyl N[4-(4-methylimidazol-1-yl)-1-bicyclo[2.2.2]octanyl] carbamate (0.072 g, 0.237 mmol) in acetone (4 mL) was added aqueous HCl (0.20 mL, 2.13 mmol) resulting in a pale yellow solution. The mixture was stirred an additional 5 hours and the solid was collected and dried under vacuo to give the title product (0.054 g, 95%) as a white solid. MS (ES+) m/z 206.2 [M+H].

1.3) General Procedure 1: Buchwald Coupling Reaction According to Scheme 1

To a solution of an intermediate 2 in NMP was added 1.1 equivalent of an intermediate 3. The reaction mixture was degased and a palladium catalyst [either dibromo-bis-(trit-ert.-butyl)-phosphine-palladium (0.1 eq. CAS185812-86-6) or tri(dibenzylidenacetonne) dipalladium(0) CAS51364-51-3 in the presence of 2-di-tert-butylphosphino-2',4',6'-triisopropylbiphenyl CAS564483-19-8] or 2-dicyclohexylphosphino-2'-(N,N-dimethylamino)biphenyl) and cesium carbonate (1.5 eq.) were added. The reaction mixture was heated at 100° C. (in a microwave or oil bath) until completion of the reaction (usually between 2 and 8 hours) and concentrated under vacuo. A purification was done either by column chromatography or reverse phase preparative HPLC to afford the desired product.

Example 1

7-(4-fluorophenyl)-N4,5,5-trimethyl-N2-[3-(5-methyl-1,3,4-oxadiazol-2-yl)-1-bicyclo[1.1.1]pentanyl]-6H-pyrrolo[2,3-d]pyrimidine-2,4-diamine

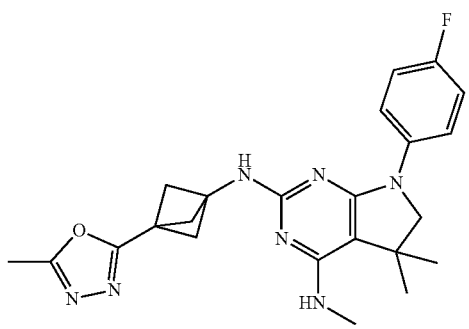 [SMILES: CNc1nc(NC23CC(c4nnc(C)o4)(C2)C3)nc2c1C(C)(C)CN2c1ccc(F)cc1]

Using the general coupling procedure 1, from 2-chloro-7-(4-fluorophenyl)-N,5,5-trimethyl-6H-pyrrolo[2,3-d]pyrimidin-4-amine (2a-1) and 3-(5-methyl-1,3,4-oxadiazol-2-yl)bicyclo[1.1.1]pentan-1-amine (3-1) was prepared 123 mg of the title compound as a white solid. MS (ES+) m/z: 436.3 [(M+H)+].

Example 2

7-(4-fluorophenyl)-N4,5,5-trimethyl-N2-[3(4-methylimidazol-1-yl)-1-bicyclo[1.1.1]pentanyl]-6H-pyrrolo[2,3-d]pyrimidine-2,4-diamine

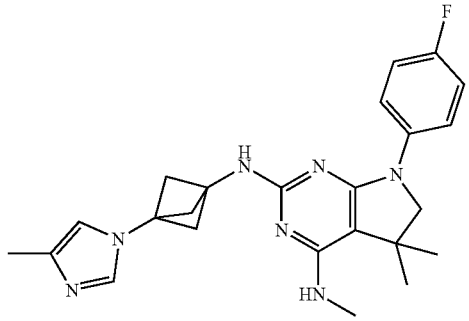 [SMILES: CNc1nc(NC23CC(n4cnc(C)c4)(C2)C3)nc2c1C(C)(C)CN2c1ccc(F)cc1]

Using the general coupling procedure 1, from 2-chloro-7-(4-fluorophenyl)-N,5,5-trimethyl-6H-pyrrolo[2,3-d]pyrimidin-4-amine (2a-1) and 3-(4-methylimidazol-1-yl)bicyclo[1.1.1]pentan-1-amine (3-2) was prepared 25 mg of the title compound as a light brown solid. MS (ES+) m/z: 434.2 [(M+H)+].

Example 3

7-(4-fluorophenyl)-N4,5,5-trimethyl-N2-[4-(4-methylimidazol-1-yl)-1-bicyclo[2.2.2]octanyl]-6H-pyrrolo[2,3-d]pyrimidine-2,4-diamine

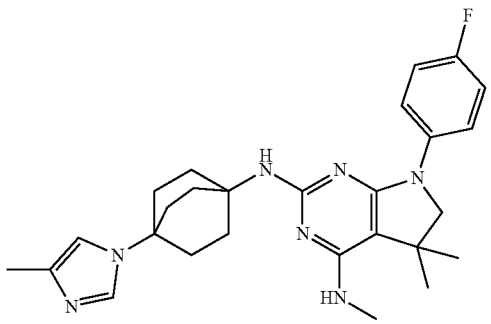 [SMILES: CNc1nc(NC23CCC(n4cnc(C)c4)(CC2)CC3)nc2c1C(C)(C)CN2c1ccc(F)cc1]

Using the general coupling procedure 1, from 2-chloro-7-(4-fluorophenyl)-N,5,5-trimethyl-6H-pyrrolo[2,3-d]pyrimidin-4-amine (2a-1) and 4-(4-methylimidazol-1-yl)bicyclo[2.2.2]octan-1-amine. hydrochloride (3-3) was prepared 59 mg of the title compound as a white solid. MS (ES+) m/z: 476.4 [(M+H)+].

Examples 4 and 5

(7R)-7-(4-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine and (7S)-7-(4-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine

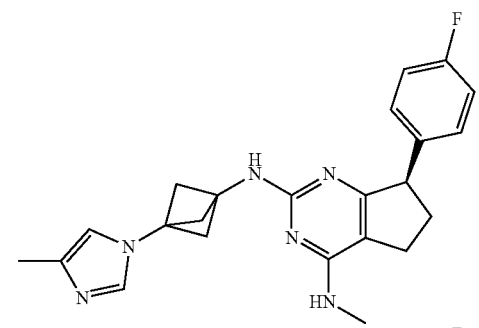

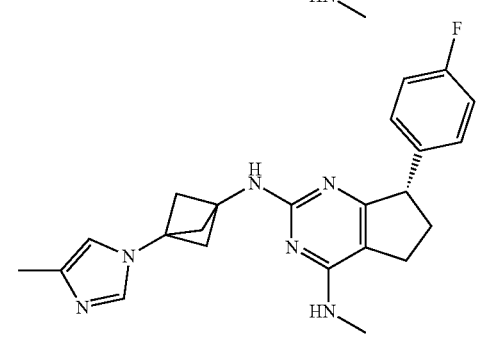

Using the general coupling procedure 1, from 2-chloro-7-(4-fluorophenyl)-N-methyl-6,7-dihydro-5H-cyclopenta[d]

pyrimidin-4-amine (2b-1) and 3-(4-methylimidazol-1-yl)bicyclo[1.1.1]pentan-1-amine (3-2) was prepared 41 mg of the racemic 7-(4-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine compound. This was then subjected to chiral HPLC separation giving both enantiomeres (7R)-7-(4-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine (10 mg) as a white solid. MS (ES+) m/z: 405.3 [(M+H)+] and (7S)-7-(4-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine (11 mg) as a white solid. MS (ES+) m/z: 405.3 [(M+H)+].

Examples 6 and 7

(7R)-7-(4-fluorophenyl)-N4-methyl-N2-[4-(4-methylimidazol-1-yl)-1-bicyclo[2.2.2]octanyl]-6,7-dihydro-5H-cyclopenta[d]pyrimidine-2,4-diamine and (7S)-7-(4-fluorophenyl)-N4-methyl-N2-[4-(4-methylimidazol-1-yl)-1-bicyclo[2.2.2]octanyl]-6,7-dihydro-5H-cyclopenta[d]pyrimidine-2,4-diamine

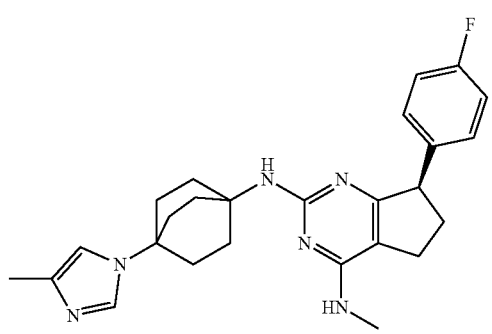

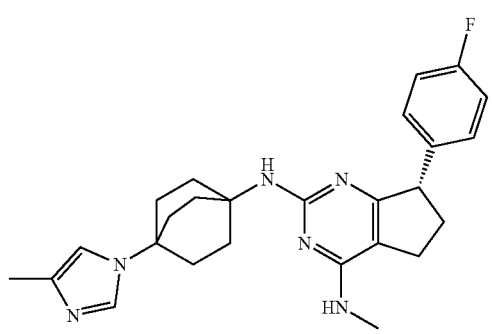

Using the general coupling procedure 1, from 2-chloro-7-(4-fluorophenyl)-N-methyl-6,7-dihydro-5H-cyclopenta[d]pyrimidin-4-amine (2b-1) and 4-(4-methylimidazol-1-yl)bicyclo[2.2.2]octan-1-amine. hydrochloride (3-3) was prepared 19 mg of the racemic 7-(4-fluorophenyl)-N4-methyl-N2-[4-(4-methylimidazol-1-yl)-1-bicyclo[2.2.2]octanyl]-6,7-dihydro-5H-cyclopenta[d]pyrimidine-2,4-diamine compound. This was then subjected to chiral HPLC separation giving both enantiomeres (7R)-7-(4-fluorophenyl)-N4-methyl-N2-[4-(4-methylimidazol-1-yl)-1-bicyclo[2.2.2]octanyl]-6,7-dihydro-5H-cyclopenta[d]pyrimidine-2,4-diamine (5.3 mg) as a white solid. MS (ES+) m/z: 447.3 [(M+H)+] and (7S)-7-(4-fluorophenyl)-N4-methyl-N2-[4-(4-methylimidazol-1-yl)-1-bicyclo[2.2.2]octanyl]-6,7-dihydro-5H-cyclopenta[d]pyrimidine-2,4-diamine (5.1 mg) as a white solid. MS (ES+) m/z: 447.3 [(M+H)+].

Examples 8 and 9

(7R)-7-(3-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine and (7S)-7-(3-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine

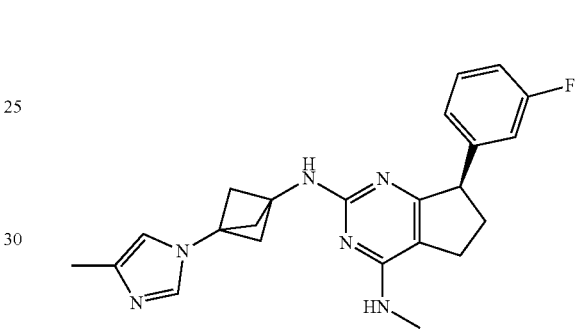

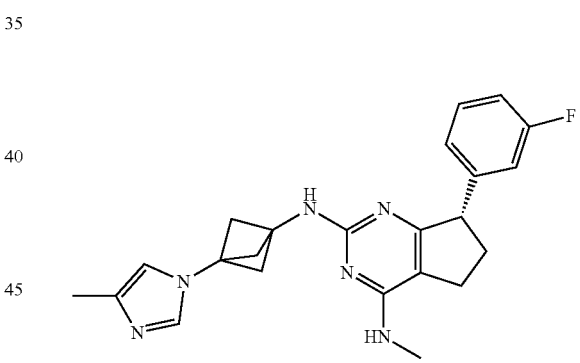

Using the general coupling procedure 1, from 2-chloro-7-(3-fluorophenyl)-N-methyl-6,7-dihydro-5H-cyclopenta[d]pyrimidin-4-amine (2b-2) and 3-(4-methylimidazol-1-yl)bicyclo[1.1.1]pentan-1-amine (3-2) was prepared 55 mg of the racemic 7-(3-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine compound. This was then subjected to chiral HPLC separation giving both enantiomeres (7R)-7-(3-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine (17 mg) as a white solid. MS (ES+) m/z: 405.3 [(M+H)+] and (7S)-7-(3-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine (16 mg) as a white solid. MS (ES+) m/z: 405.3 [(M+H)+].

Example 10

7-(4-fluorophenyl)-N4-methyl-N2-[3-(4-methylimidazol-1-yl)-1-bicyclo[1.1.1]pentanyl]-5,6-dihydropyrrolo[2,3-d]pyrimidine-2,4-diamine

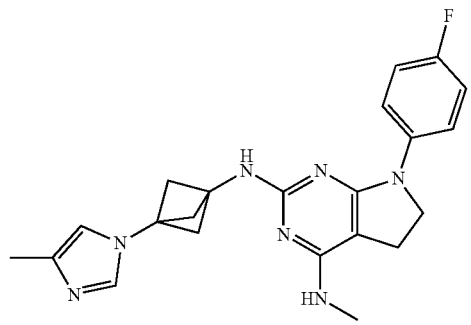 [SMILES: CNc1nc(NC23CC(n4cnc(C)c4)(C2)C3)nc2c1CCN2c1ccc(F)cc1]

Using the general coupling procedure 1, from 2-chloro-7-(4-fluorophenyl)-N-methyl-5,6-dihydropyrrolo[2,3-d]pyrimidin-4-amine (2c-1) and 3-(4-methylimidazol-1-yl)bicyclo[1.1.1]pentan-1-amine (3-2) was prepared 5 mg of the title compound as a white solid. MS (ES+) m/z: 406.3 [(M+H)$^+$].

Example 11

7-(3,5-difluorophenyl)-N4-methyl-N2-[3-(4-methylimidazol-1-yl)-1-bicyclo[1.1.1]pentanyl]-5,6-dihydropyrrolo[2,3-d]pyrimidine-2,4-diamine

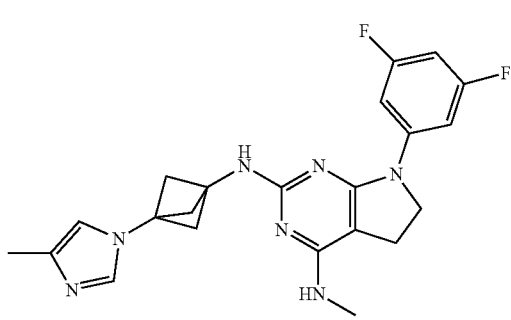 [SMILES: CNc1nc(NC23CC(n4cnc(C)c4)(C2)C3)nc2c1CCN2c1cc(F)cc(F)c1]

Using the general coupling procedure 1, from 2-chloro-7-(3,5-difluorophenyl)-N-methyl-5,6-dihydropyrrolo[2,3-d]pyrimidin-4-amine (2c-2) and 3-(4-methylimidazol-1-yl)bicyclo[1.1.1]pentan-1-amine (3-2) was prepared 17 mg of the title compound as a white solid. MS (ES+) m/z: 424.4 [(M+H)$^+$].

Example 12

7-(2,4-difluorophenyl)-N4-methyl-N2-[3-(4-methylimidazol-1-yl)-1-bicyclo[1.1.1]pentanyl]-5,6-dihydropyrrolo[2,3-d]pyrimidine-2,4-diamine

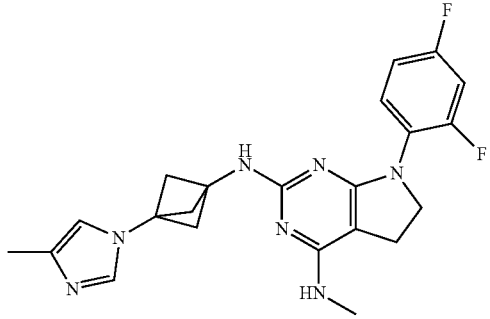 [SMILES: CNc1nc(NC23CC(n4cnc(C)c4)(C2)C3)nc2c1CCN2c1ccc(F)cc1F]

Using the general coupling procedure 1, from 2-chloro-7-(2,4-difluorophenyl)-N-methyl-5,6-dihydropyrrolo[2,3-d]pyrimidin-4-amine (2c-3) and 3-(4-methylimidazol-1-yl)bicyclo[1.1.11]pentan-1-amine (3-2) was prepared 5 mg of the title compound as a white solid. MS (ES+) m/z: 424.3 [(M+H)$^+$].

Example 13

7-(3-chloro-5-fluoro-phenyl)-N4-methyl-N2-[3-(4-methylimidazol-1-yl)-1-bicyclo[1.1.1]pentanyl]-5,6-dihydropyrrolo[2,3-d]pyrimidine-2,4-diamine

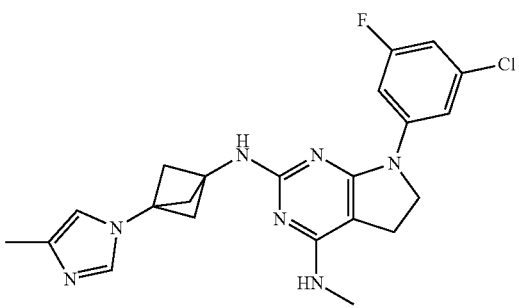 [SMILES: CNc1nc(NC23CC(n4cnc(C)c4)(C2)C3)nc2c1CCN2c1cc(F)cc(Cl)c1]

Using the general coupling procedure 1, from 2-chloro-7-(3-chloro-5-fluoro-phenyl)-N-methyl-5,6-dihydropyrrolo[2,3-d]pyrimidin-4-amine (2c-4) and 3-(4-methylimidazol-1-yl)bicyclo[1.1.1]pentan-1-amine (3-2) was prepared 10 mg of the title compound as a white solid. MS (ES+) m/z: 440.3 [(M+H)$^+$].

Example 14

7-(4-fluorophenyl)-N4-methyl-N2-[4-(4-methylimidazol-1-yl)-1-bicyclo[2.2.2]octanyl]-5,6-dihydropyrrolo[2,3-d]pyrimidine-2,4-diamine

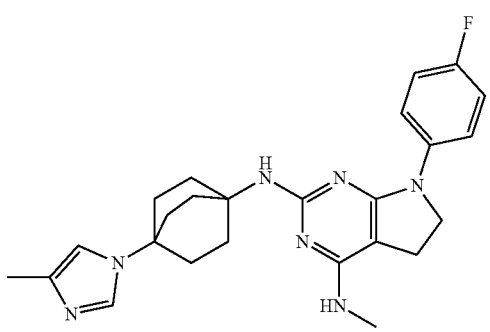 [SMILES: CNc1nc(NC23CCC(n4cnc(C)c4)(CC2)CC3)nc2c1CCN2c1ccc(F)cc1]

Using the general coupling procedure 1, from 2-chloro-7-(4-fluorophenyl)-N-methyl-5,6-dihydropyrrolo[2,3-d]pyrimidin-4-amine (2c-1) and 4-(4-methylimidazol-1-yl)bicyclo[2.2.2]octan-1-amine. hydrochloride (3-3) was prepared 3 mg of the title compound as a white solid. MS (ES+) m/z: 448.4 [(M+H)$^+$].

Example 15

N4-methyl-N2-[3-(4-methylimidazol-1-yl)-1-bicyclo[1.1.1]pentanyl]-7-(2,3,4-trifluorophenyl)-5,6-dihydropyrrolo[2,3-d]pyrimidine-2,4-diamine

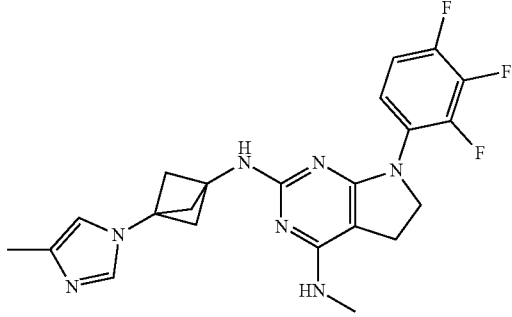 [SMILES: CNc1nc(NC23CC(n4cnc(C)c4)(C2)C3)nc2c1CCN2c1ccc(F)c(F)c1F]

Using the general coupling procedure 1, from 2-chloro-N-methyl-7-(2,3,4-trifluorophenyl)-5,6-dihydropyrrolo[2,3-d]pyrimidin-4-amine (2c-5) and 3-(4-methylimidazol-1-yl)bicyclo[1.1.1]pentan-1-amine (3-2) was prepared 20 mg of the title compound as a white solid. MS (ES+) m/z: 442.4 [(M+H)$^+$].

Example 16

7-(2-fluorophenyl)-N4-methyl-N2-[3-(4-methylimidazol-1-yl)-1-bicyclo[1.1.1]pentanyl]-5,6-dihydropyrrolo[2,3-d]pyrimidine-2,4-diamine

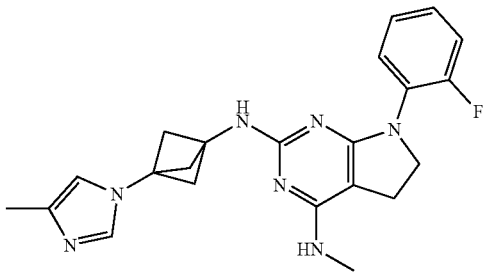 [SMILES: CNc1nc(NC23CC(n4cnc(C)c4)(C2)C3)nc2c1CCN2c1ccccc1F]

Using the general coupling procedure 1, from 2-chloro-7-(2-fluorophenyl)-N-methyl-5,6-dihydropyrrolo[2,3-d]pyrimidin-4-amine (2c-6) and 3-(4-methylimidazol-1-yl)bicyclo[1.1.1]pentan-1-amine (3-2) was prepared 35 mg of the title compound as a white solid. MS (ES+) m/z: 406.4 [(M+H)$^+$].

Example 17

7-(2,3-difluorophenyl)-N4-methyl-N2-[3-(4-methylimidazol-1-yl)-1-bicyclo[1.1.1]pentanyl]-5,6-dihydropyrrolo[2,3-d]pyrimidine-2,4-diamine

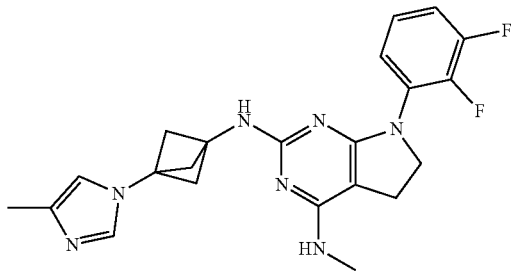 [SMILES: CNc1nc(NC23CC(n4cnc(C)c4)(C2)C3)nc2c1CCN2c1cccc(F)c1F]

Using the general coupling procedure 1, from 2-chloro-7-(2,3-difluorophenyl)-N-methyl-5,6-dihydropyrrolo[2,3-d]pyrimidin-4-amine (2c-7) and 3-(4-methylimidazol-1-yl)bicyclo[1.1.1]pentan-1-amine (3-2) was prepared 24 mg of the title compound as a white solid. MS (ES+) m/z: 424.3 [(M+H)$^+$].

2) Biological Examples 2.1) Assay Procedure: Cellular γ-Secretase Assay

The compounds were investigated in accordance with the test given hereinafter.

Human neuroglioma H4 cells overexpressing human APP695 with the Swedish double mutation (K595N/M596L) were plated at 30,000 cells/well/100 µl in 96-well plates in IMDM media containing 10% FCS, 0.2 mg/l Hygromycin B and incubated at 37° C., 5% CO$_2$. 3-4 hr post plating, compounds are a diluted in media and 50 µl is added as 1.5-fold concentrate to achieve the final concentration. Compound incubation is performed for 24 hr. Final doses typically range from 4 µM down to 0.0013 µM in half-log steps resulting in a eight point dose response curve.

Appropriate controls using vehicle only and reference compound were applied to this assay. The final concentration of Me$_2$SO was 0.4%.

After incubation at 37° C., 5% CO$_2$, the supernatant was subjected to quantification of secreted Aβ42 by the means of an AlphaLisa® assay kit (Human Amyloid beta 1-42 Kit, Perkin Elmer Inc.). 20 µl of the cell culture supernatant was transferred to an assay plate. Then 10 µl of a mixture of the AlphaLisa® coupled capture antibody and the biotinylated detection antibody was added and incubated for 3 hours at room temperature while softly shaking the assay plate. After a further addition of 20 µl of the Donor beads the assay plate was incubated for 30 min at room temperature and constant shaking without exposure to direct light. The assay plate was then read on a Paradigm AlphaLisa® Reader using the build-in program with excitation at 680 nm and emission at 570 nm.

The measured signals were then used to calculate IC$_{50}$ values for inhibition of Aβ42 secretion by nonlinear regression fit analysis using XLfit 5.3 software (from IDBS Ltd).

2.2) Results

The table below shows the data for all compounds for the inhibition of Aβ42 secretion:

| Example No. | Aβ42 IC$_{50}$ (uM) | Example No. | Aβ42 IC$_{50}$ (uM) |
|---|---|---|---|
| 1 | 0.032 | 2 | 0.006 |
| 3 | 0.096 | 4 | 0.068 |
| 5 | 0.029 | 6 | 0.167 |
| 7 | 0.526 | 8 | 0.031 |
| 9 | 0.029 | 10 | 0.005 |
| 11 | 0.004 | 12 | 0.008 |
| 13 | 0.005 | 14 | 0.092 |
| 15 | 0.005 | 16 | 0.012 |
| 17 | 0.005 | | |

The invention claimed is:

1. A compound of formula (I)

wherein:
each R$^1$ is independently selected from hydrogen and halogen;
n is 1, 2 or 3;
R$^2$ is hydrogen or methyl;
R$^3$ is selected from is selected from and
X is nitrogen or carbon;
or a pharmaceutically acceptable salt thereof.

2. A medicament containing one or more compounds as recited in claim 1 and a pharmaceutically acceptable excipient.

3. A method for inhibiting Amyloid β secretion in a subject in need thereof, wherein the method comprises administering to the subject an effective amount of a compound according to claim 1, or a pharmaceutically acceptable salt thereof.

4. The method of claim 3, wherein the subject has a disease selected from the group consisting of: Alzheimer's disease, cerebral amyloid angiopathy, hereditary cerebral hemorrhage with amyloidosis-Dutch-type, multi-infarct dementia, dementia pugilistica or Down syndrome.

5. A process for preparing a compound of formula (I) as defined in claim 1, which process comprises:
reacting a compound of formula 2 with a compound of formula 3

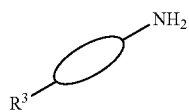

to form the compound of formula (I)

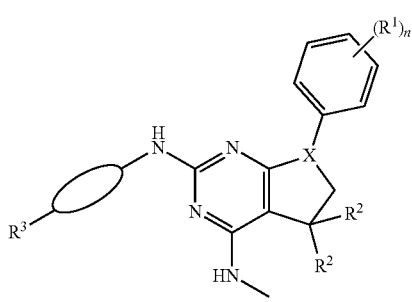

wherein $R^1$, $R^2$, $R^3$, n,

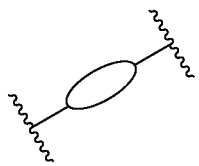

and X are as defined in claim 1, and optionally converting the compounds obtained into pharmaceutically acceptable salts thereof.

6. A compound prepared by a process as recited in claim 5.

7. A compound of formula (I-a), wherein:
each $R^1$ is independently selected from hydrogen and halogen;
n is 1, 2 or 3;
$R^2$ is hydrogen or methyl; and
$R^3$ is selected from

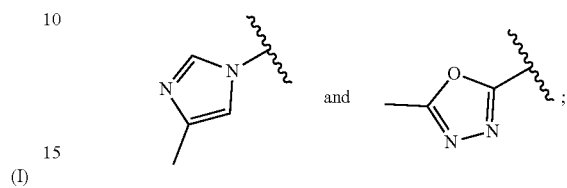

or a pharmaceutically acceptable salt thereof.

8. A compound according to claim 7, selected from:

7-(4-fluorophenyl)-N4,5,5-trimethyl-N2-[3-(5-methyl-1,3,4-oxadiazol-2-yl)-1-bicyclo[1.1.1]pentanyl]-6H-pyrrolo[2,3-d]pyrimidine-2,4-diamine;

7-(4-fluorophenyl)-N4,5,5-trimethyl-N2-[3-(4-methylimidazol-1-yl)-1-bicyclo[1.1.1]pentanyl]-6H-pyrrolo[2,3-d]pyrimidine-2,4-diamine;

7-(4-fluorophenyl)-N4-methyl-N2-[3-(4-methylimidazol-1-yl)-1-bicyclo[1.1.1]pentanyl]-5, 6-dihydropyrrolo[2,3-d]pyrimidine-2,4-diamine;

7-(3,5-difluorophenyl)-N4-methyl-N2-[3-(4-methylimidazol-1-yl)-1-bicyclo[1.1.1]pentanyl]-5, 6-dihydropyrrolo[2,3-d]pyrimidine-2,4-diamine;

7-(2,4-difluorophenyl)-N4-methyl-N2-[3-(4-methylimidazol-1-yl)-1-bicyclo[1.1.1]pentanyl]-5,6-dihydropyrrolo[2,3-d]pyrimidine-2,4-diamine;

7-(3-chloro-5-fluoro-phenyl)-N4-methyl-N2-[3-(4-methylimidazol-1-yl)-1-bicyclo[1.1.1]pentanyl]-5,6-dihydropyrrolo[2,3-d]pyrimidine-2,4-diamine;

N4-methyl-N2-[3-(4-methylimidazol-1-yl)-1-bicyclo[1.1.1]pentanyl]-7-(2,3, 4-trifluorophenyl)-5,6-dihydropyrrolo[2,3-d]pyrimidine-2,4-diamine;

7-(2-fluorophenyl)-N4-methyl-N2-[3-(4-methylimidazol-1-yl)-1-bicyclo[1.1.1]pentanyl]-5, 6-dihydropyrrolo[2,3-d]pyrimidine-2,4-diamine; and 7-(2,3-difluorophenyl)-N4-methyl-N2-[3-(4-methylimidazol-1-yl)-1-bicyclo[1.1.1]pentanyl]-5, 6-dihydropyrrolo[2,3-d]pyrimidine-2,4-diamine;

or a pharmaceutically acceptable salt thereof.

9. A compound of formula (I-b),

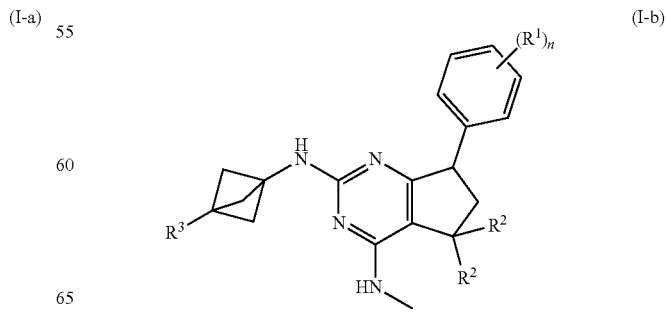

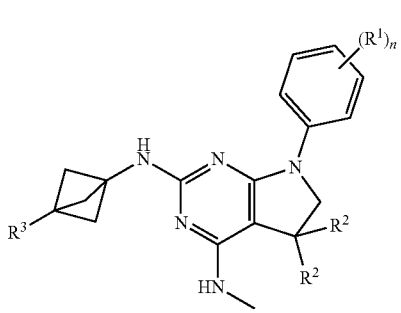

wherein:

each R¹ is independently selected from hydrogen and halogen;

n is 1, 2 or 3;

R² is hydrogen or methyl; and

R³ is selected from

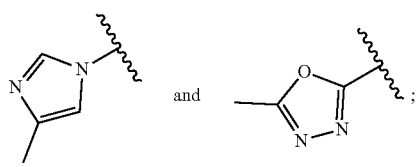

or a pharmaceutically acceptable salt thereof.

10. A compound according to claim 9, selected from:

(7R)-7-(4-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine;

(7S)-7-(4-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine;

(7R)-7-(3-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine; and (7S)-7-(3-fluorophenyl)-N4-methyl-N2-[3-(4-methylimidazol-1-yl)-1-bicyclo[1.1.1]pentanyl]-6,7-dihydro-5H-cyclopenta[d]pyrimidine-2,4-diamine;

or a pharmaceutically acceptable salt thereof.

11. A compound of formula (I-c),

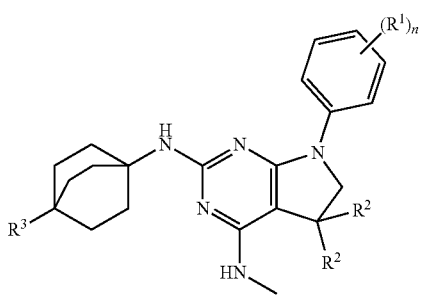

(I-c)

wherein:

each R¹ is independently selected from hydrogen and halogen;

n is 1, 2 or 3;

R² is hydrogen or methyl; and

R³ is selected from

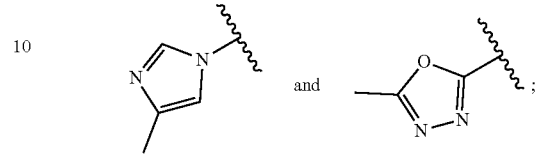

or a pharmaceutically acceptable salt thereof.

12. A compound according to claim 11, selected from:

7-(4-fluorophenyl)-N4,5,5-trimethyl-N2-[4-(4-methylimidazol-1-yl)-1-bicyclo[2.2.2]octanyl]-6H-pyrrolo[2,3-d]pyrimidine-2,4-diamine; and 7-(4-fluorophenyl)-N4-methyl-N2-[4-(4-methylimidazol-1-yl)-1-bicyclo[2.2.2]octanyl]-5,6-dihydropyrrolo[2,3-d]pyrimidine-2,4-diamine;

or a pharmaceutically acceptable salt thereof.

13. A compound of formula (I-d),

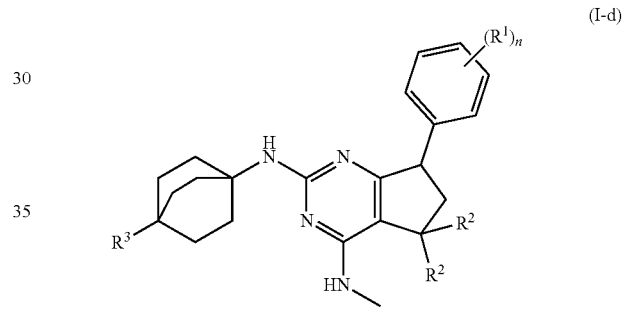

(I-d)

wherein:

each R¹ is independently selected from hydrogen and halogen;

n is 1, 2 or 3;

R² is hydrogen or methyl; and

R³ is selected from

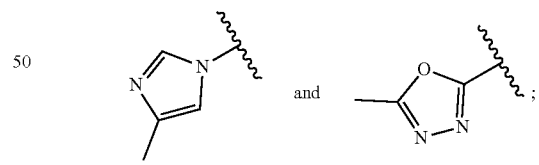

or a pharmaceutically acceptable salt thereof.

14. The compound according to claim 13, selected from:

(7R)-7-(4-fluorophenyl)-N4-methyl-N2-[4-(4-methylimidazol-1-yl)-1-bicyclo[2.2.2]octanyl]-6,7-dihydro-5H-cyclopenta[d]pyrimidine-2,4-diamine; and (7S)-7-(4-fluorophenyl)-N4-methyl-N2-[4-(4-methylimidazol-1-yl)-1-bicyclo[2.2.2]octanyl]-6,7-dihydro-5H-cyclopenta[d]pyrimidine-2,4-diamine;

or a pharmaceutically acceptable salt thereof.

* * * * *